United States Patent
Snow et al.

(10) Patent No.: US 11,058,351 B2
(45) Date of Patent: Jul. 13, 2021

(54) METHOD FOR IMPROVING HEAD POSITION OF OSTEOPOROSIS PATIENTS

(71) Applicants: Judy Sibille Snow, Los Altos, CA (US); Robert James Snow, Los Altos, CA (US)

(72) Inventors: Judy Sibille Snow, Los Altos, CA (US); Robert James Snow, Los Altos, CA (US)

( * ) Notice: Subject to any disclaimer, the term of this patent is extended or adjusted under 35 U.S.C. 154(b) by 210 days.

(21) Appl. No.: 15/883,605

(22) Filed: Jan. 30, 2018

(65) Prior Publication Data
US 2018/0146914 A1    May 31, 2018

Related U.S. Application Data

(63) Continuation of application No. 13/777,423, filed on Feb. 26, 2013, now abandoned.

(60) Provisional application No. 61/727,800, filed on Nov. 19, 2012.

(51) Int. Cl.
*A61B 5/00* (2006.01)
*A61B 5/11* (2006.01)
*A61B 5/021* (2006.01)

(52) U.S. Cl.
CPC .............. *A61B 5/486* (2013.01); *A61B 5/112* (2013.01); *A61B 5/1121* (2013.01); *A61B 5/4833* (2013.01); *A61B 5/7405* (2013.01); *A61B 5/021* (2013.01)

(58) Field of Classification Search
None
See application file for complete search history.

(56) References Cited

U.S. PATENT DOCUMENTS

| | | | |
|---|---|---|---|
| 4,316,641 A | 2/1982 | Weise et al. | 303/92 |
| 4,392,830 A | 7/1983 | Salzman | A63B 69/00 434/258 |
| 4,906,193 A | 3/1990 | McMullen | G09B 19/00 273/DIG. 27 |
| 5,158,089 A * | 10/1992 | Swezey | A61B 5/1071 340/573.7 |
| 5,474,083 A | 12/1995 | Church et al. | 128/733 |
| 5,749,838 A * | 5/1998 | Kline | A61B 5/1077 340/573.7 |
| 5,853,005 A | 12/1998 | Scanlon | A61B 5/113 29/235.5 |

(Continued)

FOREIGN PATENT DOCUMENTS

EP  0207258  5/1986

OTHER PUBLICATIONS

LUMOback product, downloaded from http://www.lumoback.com/?x-saying on Nov. 16, 2012.

*Primary Examiner* — Carl H Layno
*Assistant Examiner* — Manolis Pahakis
(74) *Attorney, Agent, or Firm* — John H. Runnels

(57) ABSTRACT

An apparatus is disclosed that comprises a sensor to detect a medical condition; a processor to evaluate the signals from the sensor; an input device and read/write medium to record cues that correspond to the various condition(s) detected by the sensor; and an audio output device to play prerecorded audio cues when a particular medical condition is detected. The audio cue provides a unique reminder message to encourage a person to take a certain action that is healthy.

7 Claims, 4 Drawing Sheets

(56) References Cited

U.S. PATENT DOCUMENTS

| | | | | |
|---|---|---|---|---|
| 5,916,181 A | 6/1999 | Socci | A42B 3/0433 | |
| | | | 600/595 | |
| 5,919,149 A * | 7/1999 | Allum | A61B 5/1116 | |
| | | | 600/595 | |
| 5,978,972 A | 11/1999 | Stewart | A42B 3/046 | |
| | | | 2/422 | |
| 6,005,548 A | 12/1999 | Latypov | A63F 13/00 | |
| | | | 345/156 | |
| 6,119,516 A * | 9/2000 | Hock | A61B 5/1121 | |
| | | | 600/547 | |
| 6,176,837 B1 | 1/2001 | Foxlin | G01C 21/165 | |
| | | | 128/897 | |
| 6,734,834 B1 | 5/2004 | Baram | A61B 5/1101 | |
| | | | 345/156 | |
| 7,114,451 B2 | 10/2006 | Albrich et al. | 105/149.2 | |
| 7,369,345 B1 | 5/2008 | Li et al. | 360/75 | |
| 7,430,673 B2 | 9/2008 | Kardach et al. | 713/300 | |
| D580,488 S | 11/2008 | Estevez | D19/2 | |
| 7,634,379 B2 * | 12/2009 | Noble | A61B 5/1116 | |
| | | | 702/141 | |
| 8,206,325 B1 * | 6/2012 | Najafi | A61B 5/1116 | |
| | | | 600/595 | |
| 8,308,562 B2 | 11/2012 | Patton | A63F 13/10 | |
| | | | 434/128 | |
| 8,414,507 B2 * | 4/2013 | Asada | A61B 5/4023 | |
| | | | 600/595 | |
| 8,773,256 B2 * | 7/2014 | Ten Kate | G08B 21/04 | |
| | | | 340/539.11 | |
| 9,198,575 B1 * | 12/2015 | Blacutt | G06K 9/00845 | |
| 9,345,609 B2 * | 5/2016 | Hyde | A61F 5/32 | |
| 9,406,211 B2 * | 8/2016 | Sahiholnasab | A61B 5/6805 | |
| 9,588,582 B2 * | 3/2017 | Connor | A61B 5/1126 | |
| 9,607,498 B2 * | 3/2017 | Osorio | A61B 5/0205 | |
| 9,934,668 B2 * | 4/2018 | Zhang | A61B 5/7246 | |
| 10,307,084 B2 * | 6/2019 | Forth | A61B 5/1117 | |
| 10,314,520 B2 * | 6/2019 | Hauenstein | A61B 5/1118 | |
| 10,314,733 B2 * | 6/2019 | Hyde | A61F 5/34 | |
| 2002/0045438 A1 | 4/2002 | Tagawa et al. | 455/412 | |
| 2002/0133377 A1 | 9/2002 | Brown | 705/3 | |
| 2003/0088294 A1 | 5/2003 | Gesotti | A61N 1/36003 | |
| | | | 607/45 | |
| 2003/0109289 A1 | 6/2003 | Shuhei | 455/567 | |
| 2004/0015103 A1 | 1/2004 | Aminian | A61B 5/1116 | |
| | | | 600/595 | |
| 2005/0126026 A1 | 6/2005 | Townsend | A61B 5/1116 | |
| | | | 33/512 | |
| 2006/0064037 A1 | 3/2006 | Shalon | A61B 5/0006 | |
| | | | 600/586 | |
| 2006/0259472 A1 | 11/2006 | MacClellan | G06Q 10/06 | |
| 2007/0015611 A1 * | 1/2007 | Noble | A61B 5/1116 | |
| | | | 473/450 | |
| 2007/0027369 A1 | 2/2007 | Pagnacco | A61B 5/1071 | |
| | | | 600/301 | |
| 2007/0032748 A1 * | 2/2007 | McNeil | A61B 5/1038 | |
| | | | 600/595 | |
| 2007/0112287 A1 | 5/2007 | Fancourt | A61B 5/1038 | |
| | | | 600/595 | |
| 2007/0136102 A1 | 6/2007 | Rodgers | 705/3 | |
| 2007/0161912 A1 | 7/2007 | Zhang | A61B 5/0215 | |
| | | | 600/483 | |
| 2007/0197881 A1 | 8/2007 | Wolf et al. | 600/300 | |
| 2007/0273504 A1 | 11/2007 | Tran | A61B 5/0022 | |
| | | | 340/539.12 | |
| 2007/0299362 A1 | 12/2007 | Epley | A61B 5/4863 | |
| | | | 600/559 | |
| 2008/0039778 A1 | 2/2008 | Goldie et al. | 604/67 | |
| 2008/0146890 A1 | 6/2008 | LeBoeuf | A61B 5/0059 | |
| | | | 600/300 | |
| 2008/0319352 A1 * | 12/2008 | Chow | A61B 5/1116 | |
| | | | 600/595 | |
| 2009/0012433 A1 * | 1/2009 | Fernstrom | A61B 5/411 | |
| | | | 600/593 | |
| 2009/0030350 A1 | 1/2009 | Yang | A61B 5/1038 | |
| | | | 600/595 | |
| 2009/0192414 A1 * | 7/2009 | Yasuhara | A61H 3/00 | |
| | | | 600/587 | |
| 2009/0312817 A1 | 12/2009 | Hogle et al. | 607/54 | |
| 2009/0312973 A1 | 12/2009 | Hatlestad | A61B 5/103 | |
| | | | 702/85 | |
| 2010/0205541 A1 * | 8/2010 | Rapaport | G06Q 10/10 | |
| | | | 715/753 | |
| 2011/0021320 A1 | 1/2011 | Lenhardt | A61H 3/00 | |
| | | | 482/9 | |
| 2011/0063114 A1 * | 3/2011 | Ikoyan | A63B 21/4007 | |
| | | | 340/573.7 | |
| 2011/0121976 A1 | 5/2011 | Johns | A61B 3/113 | |
| | | | 340/576 | |
| 2011/0125063 A1 | 5/2011 | Shalon et al. | 600/590 | |
| 2011/0132378 A1 | 6/2011 | Levendowski et al. | 128/848 | |
| 2011/0208444 A1 | 8/2011 | Solinsky | 702/41 | |
| 2011/0246123 A1 | 10/2011 | DelloStritto et al. | 702/141 | |
| 2011/0263997 A1 | 10/2011 | Corn | 600/529 | |
| 2012/0075464 A1 * | 3/2012 | Derenne | H04N 7/185 | |
| | | | 348/135 | |
| 2013/0013087 A1 * | 1/2013 | Aliakseyeu | G06F 3/0487 | |
| | | | 700/83 | |
| 2013/0015976 A1 | 1/2013 | Chang | A61B 5/0002 | |
| | | | 340/573.7 | |
| 2013/0158940 A1 | 6/2013 | Crane, III | G01C 9/02 | |
| | | | 702/141 | |
| 2013/0190658 A1 * | 7/2013 | Flaction | A61B 5/1038 | |
| | | | 600/595 | |
| 2013/0265169 A1 | 10/2013 | Mates | G02C 11/10 | |
| | | | 340/686.1 | |
| 2013/0311134 A1 | 11/2013 | Kordarl | G06F 17/10 | |
| | | | 702/160 | |
| 2014/0114148 A1 * | 4/2014 | Shepherd | A61B 5/4266 | |
| | | | 600/301 | |
| 2014/0243686 A1 | 8/2014 | Kimmel | 600/476 | |
| 2014/0247343 A1 * | 9/2014 | Chen | A61B 5/0022 | |
| | | | 348/135 | |
| 2014/0364769 A1 * | 12/2014 | Chang | A61B 5/1116 | |
| | | | 600/595 | |
| 2015/0142381 A1 * | 5/2015 | Fitzsimmons | A47C 7/006 | |
| | | | 702/166 | |
| 2015/0364057 A1 * | 12/2015 | Catani | G16H 20/30 | |
| | | | 434/127 | |
| 2016/0066847 A1 * | 3/2016 | Sales | A61B 5/0022 | |
| | | | 600/324 | |
| 2016/0260309 A1 * | 9/2016 | Dayal | G08B 21/0446 | |
| 2017/0095692 A1 * | 4/2017 | Chang | A63B 24/0003 | |
| 2017/0103636 A1 * | 4/2017 | Tu | A61B 5/4566 | |
| 2017/0232300 A1 | 8/2017 | Tran | H04L 67/10 | |
| | | | 434/247 | |
| 2017/0258374 A1 * | 9/2017 | Ly | A61B 5/1118 | |
| 2018/0192920 A1 * | 7/2018 | Rosenblood | A61B 5/486 | |
| 2019/0090781 A1 * | 3/2019 | Selvaraj | G01P 21/00 | |
| 2019/0150795 A1 * | 5/2019 | Lu | G09B 1/06 | |

* cited by examiner

301 Desired Head Position

107

302 Undesired Head Position

107

301 Desired Head Position

107

302 Undesired Head Position

107

METHOD FOR IMPROVING HEAD POSITION OF OSTEOPOROSIS PATIENTS

CROSS-REFERENCE TO RELATED APPLICATIONS

This application is a continuation of copending U.S. nonprovisional application Ser. No. 13/777,423, filed Feb. 26, 2013, now abandoned; which claimed priority under 35 U.S.C. § 119(e) from U.S. Provisional Application Ser. No. 61/727,800, filed Nov. 19, 2012, entitled "Audio Feedback for Medical Conditions." The full disclosures of both of these priority applications are fully incorporated by reference herein.

TECHNICAL FIELD

This invention relates to the field of applications designed to monitor and provide audio feedback for human medical conditions.

BACKGROUND ART

Some people have a medical condition that is exacerbated by physical conditions. For example, some people look down habitually when they walk. This is especially noticeable in people who develop osteoporosis because their neck no longer straightens, and it is easier and more natural for them to look down. Physical therapists encourage patients to keep their head up to prevent them from getting dizzy. The consequences of dizziness can be serious, such as a fall resulting in a broken bone.

Recordable greeting cards have been disclosed (e.g., EP0207258A1 to Weigl, D580488 to Zarfas), as have a plethora of medical sensors. Some of these sensors may emit vibrations or sounds. A Lumoback product (webpage visited Nov. 16, 2012), www <dot>lumoback<dot>com/?x=saying, comprises a belt that is worn around a patient's abdomen, and that provides vibrations when the patient's lower back slouches, reminding the patient to stand up or sit up straight.

Unfortunately, the physical therapist isn't always with the patient who needs a reminder in response to a physical condition, such as to lift the head up. Although a vibration could be useful for as a reminder for a single condition, a vibration does not readily differentiate among various multiple physical conditions.

There is an unfilled need for an improved device which can both detect certain medically significant conditions and provide enhanced real-time feedback to the user to inform them of the detected medical condition, with the flexibility of providing different cues when the detected conditions are different.

DISCLOSURE OF THE INVENTION

We have invented an apparatus that comprises a sensor to detect a medical condition, or more generally a body measurement of any type, for example a condition related to the movement or position of the body or part of the body of an individual; a processor to evaluate the signals from the sensor; an optional microphone; a read/write medium to record audio cues that correspond to the various conditions detected by the sensor; and an audio output device to play prerecorded audio cues to provide immediate feedback when a particular medical condition is detected.

The elements of the apparatus need not be physically connected, but can be configured as discrete electronic devices inter-connected via wired or wireless techniques known in the art, for example infrared signals, or radio frequency (RF) signals such as Bluetooth.

MODES FOR CARRYING OUT THE INVENTION

Figure 1:
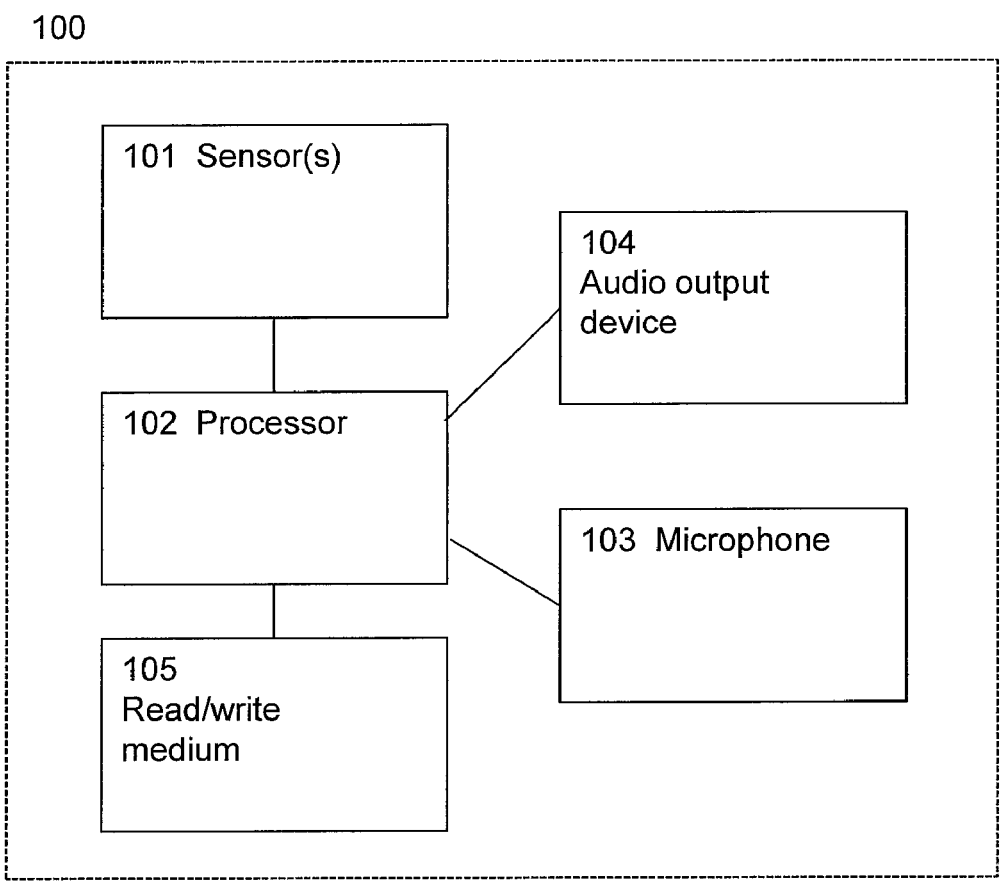
FIG. 1 illustrates schematically one embodiment of the invention.

As illustrated in the embodiment depicted in FIG. 1, system 100 comprises sensor(s) 101, processor 102, microphone 103, audio output device 104 and read/write medium 105. One or more sensor(s) 101 can detect motion, position, or other body measurements and can be used or positioned in a variety of ways. The processor 102 can be single, multi, or parallel. The read/write medium 105 can be RAM, flash, solid state, hard disk, virtual cloud storage, or other storage means. The optional microphone 103, and the audio output device 104 can be single or multi, mono or stereo, etc. The components in this configuration can be located in one or more physical packages. Connectivity can be wired, wireless, or virtual.

Figure 2:
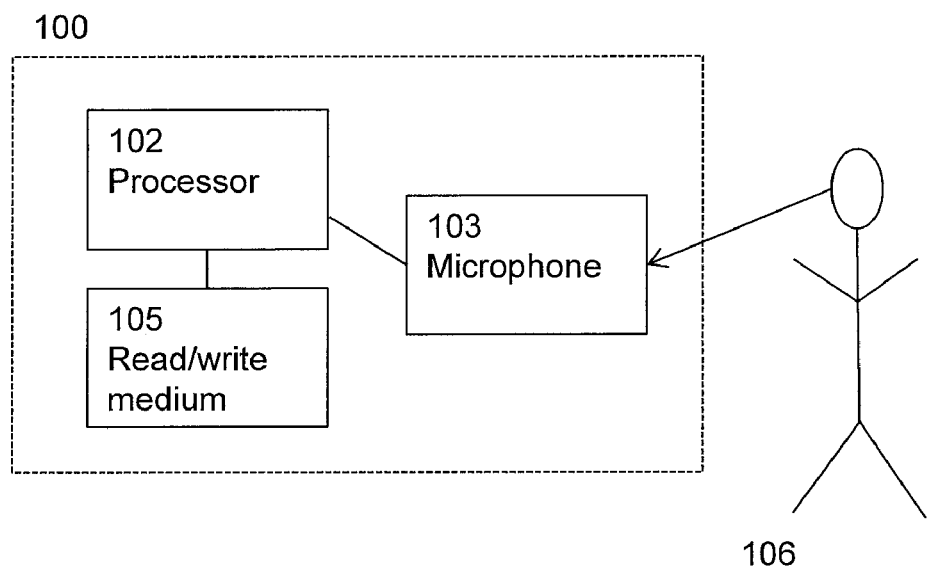
FIG. 2 illustrates schematically one embodiment of a person recording one or more audio cues for the patient.

One embodiment to record audio cues is shown in FIG. 2. Any person 106 can record cues using a microphone 103 and a processor 102 that is capable of storing the message on a read/write medium 105. The cues can be arbitrary, but it is preferred that the recordings be appropriate to the medical conditions of the specific patient. It can direct the patient 107 with specific instructions, such as "Lift your head up!" In addition, the recording can be in the patient's language of choice. An unexpected benefit is that the person who makes the recording can be a person, such as a grandchild, whose voice recording may be able to cue the patient in an especially motivating and positive way. The processor 102, microphone 103, and read/write medium 105 can be located in a single physical package or can be contained in multiple discrete packages and inter-connected electronically using any one of a number of well-known physically wired, wireless, or virtual connections. In an alternative embodiment, the system does not include a microphone. The audio cues may be recorded externally through means known in the art, for example with a voice recorder or a computer equipped with a microphone, and file(s) containing externally-recorded audio cue(s) may be uploaded to the system.

Figure 3:
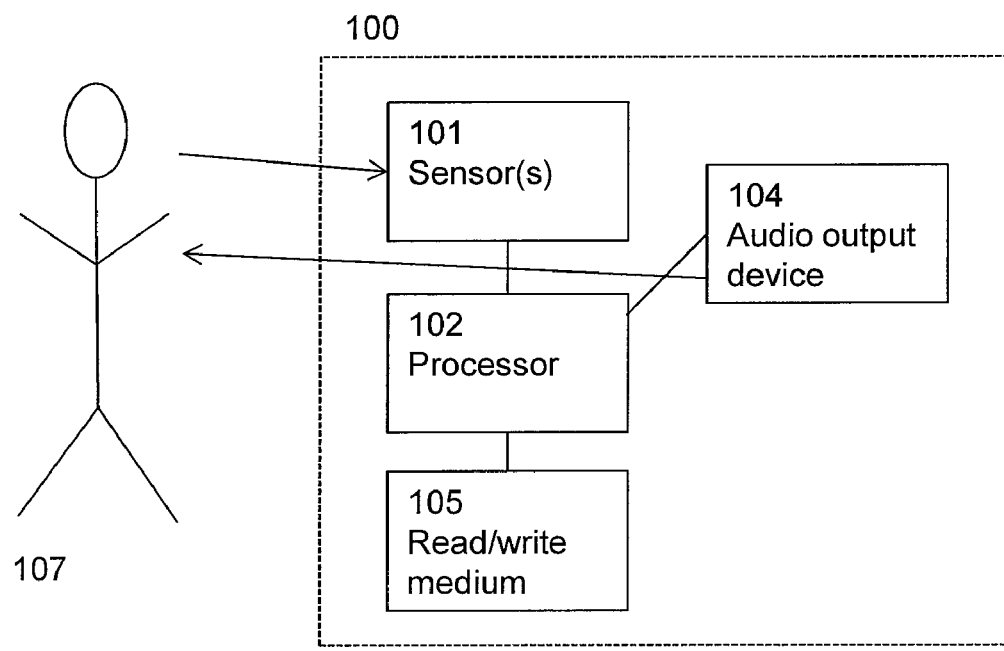
FIG. 3 illustrates schematically a patient being monitored by a sensor and receiving audio cues in accordance with one embodiment of the invention.
Figure 6:
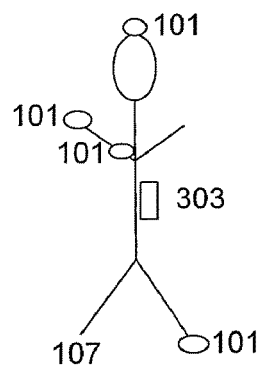
FIG. 6 illustrates schematically an alternative embodiment having multiple sensors, for example for detecting a patient's head position, hand position, blood pressure, and gait.

FIG. 3 shows one embodiment to monitor a patient 107 with sensor(s) 101. The sensor(s) 101 can be physically attached to the patient 107, or can be a remote sensor, such as a camera monitoring the patient. A processor 102 interprets data from the sensor(s) 101 and determines whether at least one medical condition is met. The medical condition can be an unhealthy change in position, pattern of motion, or other measurable body data. Multiple medical conditions can be simultaneously addressed. FIG. 6 shows an example employing multiple sensors 101: if the patient's blood pressure is detected to drop at the same time that her head position drops, she can be told to "Lie down!" to prevent a fall. Referring back to FIG. 3, the processor 102 then selects the appropriate cue from a read/write medium 105 and plays the cue on an audio output device 104 such as a speaker or headset. The sensor(s) 101, processor 102, read/write medium 105, and audio output device 104 can be located in a single physical package or can be contained in multiple discrete packages and inter-connected electronically using any one of a number of well-known physically wired, wireless, or virtual connections.

In an alternative embodiment, rather than an audio cue an output device generates another type of feedback signal, such as a buzz, vibration, light, etc.

Figure 4A:
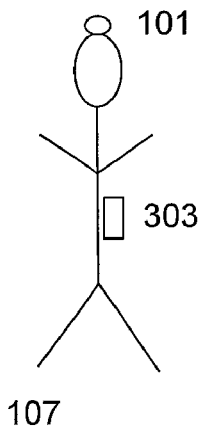
FIGS. 4A and 4B illustrate schematically an example configuration with two discrete physical devices for detecting a desirable and undesirable physical condition of a patient's head position.
Figure 4B:
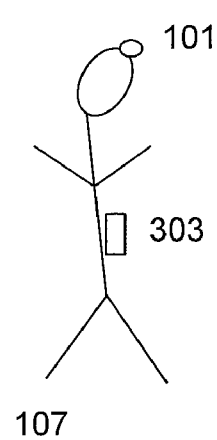

FIGS. 4A and 4B illustrate one embodiment, where a sensor 101 is attached to a hat worn on the patient's 107 head, and the rest of the hardware is contained in a package 303 attached to the patient's belt. The desired head position 301 of the patient 107 is looking straight ahead. The medical condition being detected is when the head drops or looks down, as shown by the undesired head position 302. In this example, the processor 102, microphone 103, audio output device 104, and read/write medium 105, can all be contained in an Android device or other smartphone 303, and the sensor 101 comprises an accelerometer connected wirelessly, e.g. by Bluetooth.

Figure 5A:
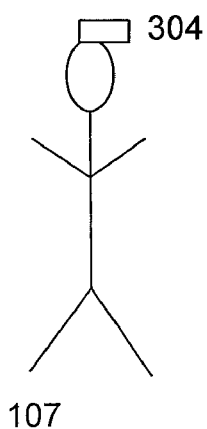
FIGS. 5A and 5B illustrate schematically a second example configuration with one discrete physical device for detecting a desirable and undesirable physical condition of a patient's head position.
Figure 5B:
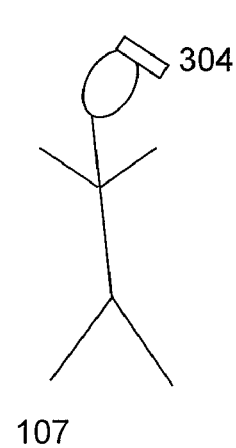

FIGS. 5A and 5B illustrate an alternative embodiment, where all hardware is in a single package 304 attached to a hat worn on the patient's 107 head. The desired head position 301 of the patient 107 is looking straight ahead. The medical condition being detected is when the head drops or looks down, as shown by the undesired head position 302. In this example, the accelerometer sensor, processor, microphone, audio output device, and read/write medium are all contained in one physical package 304, attached to patient 107's hat. In this configuration, the one package 304 could be a device running iOS, such as an iPhone. Additional embodiments could incorporate other custom or off-the-shelf hardware components in a variety of configurations and complexity.

EXAMPLE

A working device configured as depicted in FIG. 4 has been built and successfully tested to monitor and provide feedback for a patient's head position. The patient 107 showed increased compliance in keeping his head up while walking. He was much more motivated hearing his grandchild's voice in a recording, rather than another adult, such as his daughter, whom he perceived as "nagging".

In accordance with the present invention there are many additional examples of uses for sensor(s) 101 that could detect movement or position of a patient's body or body part with an accelerometer as shown in FIG. 6. For example, a sensor 101 attached to a shoe could detect a person who is dragging her foot; a medical condition that can result in tripping. A person with nervous habits such as biting their fingernails or pulling their hair (trichotillomania) could have a sensor 101 that would detect hand movements that encompass the undesired behavior. A patient could benefit from feedback on various nervous habits that might or might not rise to the level at which the nervous habits would be considered a "medical condition." Such a nervous habit is nevertheless considered a "medical condition" for purposes of this disclosure, unless context clearly indicates otherwise.

Figure 7:
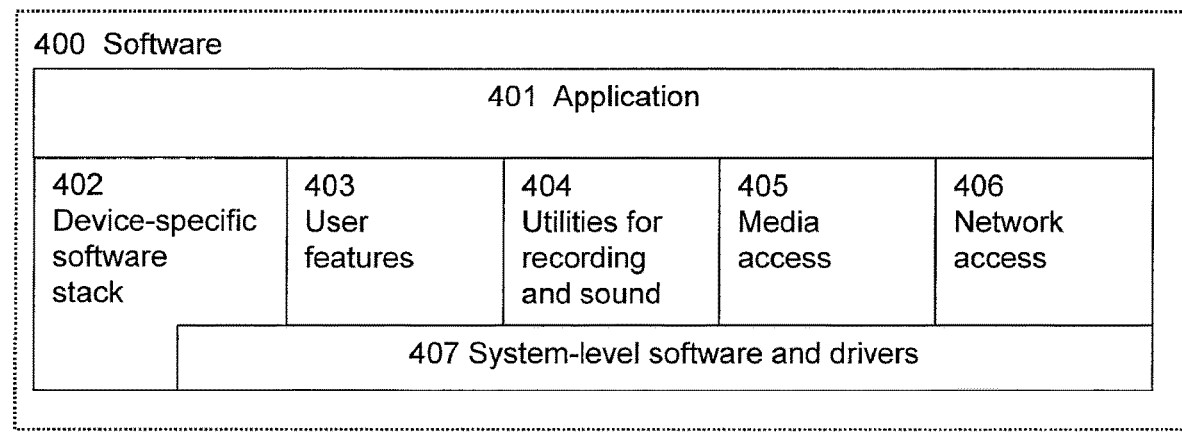
FIG. 7 illustrates schematically one embodiment of software architecture for a system to support the novel device.

FIG. 7 illustrates the components of the operating software or firmware 400 for one embodiment of the invention. The software 400 comprises the system-level software and drivers 401 for whichever physical embodiment is selected. Upon this software or firmware, a layer of software exists that can be used by the application 406 in a variety of ways as described herein. Standard utilities for recording and sound 403 are typically available in a computer system to support input from a microphone 103 for audio recording and output to an audio output device 104. A device-specific software stack 401 for a specific sensor 101 may be available commercially or through open source, or an application developer can add specific code for a particular sensor.

In one embodiment, the application 406 detects a physical condition based on a signal from the sensor(s) 101, selects the appropriate audio cue, and sends it to the audio output device 104. In an expanded embodiment, the application can also use the user features 402 of a system to implement a display showing a record of progress for the patient 107 for each sensor 101, while logging this data on the read/write medium 105. One unexpected result of using this expanded embodiment is that we have found that the audio cues can be optimized for the individual patient, based on the record of that patient's past performance or results. A second unexpected benefit is that the logged data can be exported or transmitted via standard network access 406, to other computers for analysis or distribution to medical providers, e.g., via the cloud.

The complete disclosures of all references cited in this specification are hereby incorporated by reference. In the event of an otherwise irreconcilable conflict, however, the present specification shall control.

What is claimed:

1. A method for providing a person with osteoporosis real-time feedback concerning the person's head position, said method comprising:
   (a) simultaneously taking measurements of both: (i) the position of the person's head using one or more accelerometers; and (ii) the gait of the person using one or more sensors, to ascertain when the person is walking; wherein the person is a human with osteoporosis; and wherein the person has habitual difficulty keeping the person's head up while simultaneously walking;
   (b) determining when the measurements show both of the following conditions occurring simultaneously: (i) the person's head has an undesirable downward-looking position, as determined from the accelerometer measurements; and (ii) the person is walking, as determined from the sensor measurements; and
   (c) providing real-time feedback to the person that the person's head has moved into an undesirable position while the person is simultaneously walking, by playing one or more recorded audio messages, wherein the undesirable head position is one in which the person looks down to a degree that is medically unhealthy; and wherein the one or more recorded audio messages comprise verbal instructions to the person or verbal encouragement for the person, in the person's language of choice, to prompt the person to keep the person's head in a healthy position.

2. The method of claim 1, wherein the one or more audio messages comprise one or more pre-recorded messages in the person's own voice.

3. The method of claim 1, wherein the one or more audio messages comprise one or more pre-recorded messages in the voice of someone other than the person.

4. The method of claim 1, additionally comprising the step of recording the measurements of the accelerometers and the measurements of the sensors, and analyzing those measurements to assess the person's compliance in keeping the patient's head up while the patient is walking.

5. The method of claim 4, additionally comprising the step of analyzing the recorded measurements to compare outcomes with alternative audio messages to determine which audio messages result in better compliance in keeping the patient's head up while the patient is walking; and subsequently modifying the audio messages to increase the compliance.

6. The method of claim 1, additionally comprising the steps of measuring the person's blood pressure; and of monitoring for a combination of a drop in blood pressure and an undesirable head position that indicates that the person is in danger of fainting or falling.

7. The method of claim 1, additionally comprising the step of creating one or more audio messages tailored specifically for that person.

\* \* \* \* \*